US00PP31040P2

(12) United States Plant Patent
Peterson et al.

(10) Patent No.: US PP31,040 P2
(45) Date of Patent: Nov. 12, 2019

(54) GRAPEVINE PLANT NAMED 'FRANCONIA'

(50) Latin Name: ***Vitis* hybrid**
Varietal Denomination: Franconia

(71) Applicant: Winehaven, Inc., Chisago City, MN (US)

(72) Inventors: Kevin Peterson, Chisago City, MN (US); Kyle Peterson, Chisago City, MN (US)

(73) Assignee: Winehaven, Inc., Chisago City, MN (US)

( * ) Notice: Subject to any disclaimer, the term of this patent is extended or adjusted under 35 U.S.C. 154(b) by 0 days.

(21) Appl. No.: 16/350,146

(22) Filed: Oct. 4, 2018

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./156, 205
See application file for complete search history.

(56) References Cited

U.S. PATENT DOCUMENTS

| | | | |
|---|---|---|---|
| PP4,928 | P | 11/1982 | Swenson |
| PP4,943 | P | 11/1982 | Swenson |
| PP5,588 | P | 12/1985 | Swenson |
| PP5,716 | P | 4/1986 | Swenson |
| PP5,771 | P | 7/1986 | Swenson |
| PP6,159 | P | 4/1988 | Reisch et al. |
| PP6,160 | P | 4/1988 | Reisch et al. |
| PP7,860 | P | 5/1992 | Reisch et al. |
| PP11,012 | P | 7/1999 | Reisch et al. |
| PP13,309 | P2 | 12/2002 | Clark et al. |
| PP14,617 | P3 | 3/2004 | Luby et al. |
| PP16,115 | P3 | 11/2005 | McKenry |
| PP16,478 | P3 | 4/2006 | Luby et al. |
| PP17,773 | P2 | 5/2007 | MacGregor |
| PP19,246 | P2 | 9/2008 | Peterson et al. |
| PP19,579 | P3 | 12/2008 | Hemstad et al. |
| PP23,376 | P3 | 2/2013 | Peterson et al. |
| PP27,872 | P3 | 4/2017 | Juneau |

*Primary Examiner* — Susan McCormick Ewoldt
*Assistant Examiner* — Karen M Redden

(57) ABSTRACT

A grapevine plant botanically known as *Vitis* hybrid 'Franconia', having a unique combination of hardiness, vigor, disease resistance, and wine quality characterized by clusters of large grapes having high sugars coupled with increased acidity, which can result in wines with a more complex mouthfeel that is useful in balancing fortified wines with relatively high alcohol content.

6 Drawing Sheets

Botanical classification: *Vitis* hybrid.
Variety denomination: 'FRANCONIA'.

BACKGROUND OF THE INVENTION

Growing wine grapes in non-traditional regions like Minnesota on a commercial scale is a relatively new endeavor because the region's mid-continental climate yields exceptionally cold winters that create challenges for the emerging wine industry. At the same time, the cold climate in Minnesota creates opportunities for the production of wines with increased acidity, which can result in a more complex mouthfeel, and be particularly useful in balancing fortified wines with relatively high alcohol content.

Currently, less than 100 wineries exist in Minnesota, extending from southern Minnesota to just south of the Canadian border. Many of these wineries produce non-grape wines from honey, rhubarb, raspberries, and the other fruit. However, several Minnesota wineries are currently managing substantial vineyard tracts. A few wineries have even received awards for wines produced by these vineyards at top international wine competitions.

Despite some success, grape growing in Minnesota is fraught with difficulties. Most European grape varieties that are grown in Minnesota, and even many "French-American hybrid" wine varieties, require protection if they are to survive the frigid winter temperatures—especially in northern Minnesota. This is usually done by removing vines from the trellises and bending them to the ground in early November, then covering the vine with soil or straw.

Although covering vines effectively insulates them from cold winter temperatures, there are a number of problems that make this practice less than satisfactory. Of primary concern is the greatly increased labor cost, which is generally prohibitive and makes it quite difficult for cold-climate vineyards to operate profitably. However, logistical challenges exist as well. For example, the trunks of the vine may break due to the fact that they become less pliable as they grow larger in diameter. If the vine does not break, fungi and bacteria may infiltrate the vine through small "stress cracks" in the trunk, causing disease. Rodents may also feed on the trunks and canes as they lay on the ground during the winter, further injuring the vine. If the vine survives the winter, great care must be taken to avoid damaging the buds when the vines are uncovered during the spring. Accordingly, for grapevines to be of high commercial value to vineyards in northern regions, it is nearly essential for varieties to be hardy enough to remain on the trellises throughout the winter months without removal and winter covering.

Fortunately, there exist good sources of tolerance to cold hardiness for breeding purposes, i.e. *Vitis riparia* and *Vitis labrusca*. These hardy grapes have a flavor that is acceptable in table wines. However, they are generally too high in acid and too unproductive to use on their own.

Some of the hardiest known wine grape varieties, 'Sabrevois' (not patented) (ES 2-1-9), and 'Frontenac' (not patented) (MN 1047), have demonstrated hardiness to at least −35 degrees F. (about −37.2 degrees C.) in central Minnesota. The 'Chisago' grape (U.S. Plant Pat. No. 19,246) and 'Nokomis' grape (U.S. Plant Pat. No. 23,376) have been shown to be winter hardy to about −40 degrees F. (about −40 degress C.). In central Minnesota, the present variety has proven that it is at least as winter hardy as these known varieties. The present variety also presents a wide variety of additional distinguishing characteristics including resistance to disease and pests, vigor, productivity, size of fruit, size of grape clusters, coloration, and flavor, hereinafter set forth in detail. Most notably, the berries of 'Franconia' are larger than both the 'Chisago' and 'Nokomis' grapes. However, the 'Franconia' generally contains less berries per cluster than both the 'Chisago' and 'Nokomis' cultivars. 'Franconia' berries along the transverse axis are 0.6 inch (15.24 mm) to 0.82 inch (about 21 mm). These berry dimensions are larger than both the 'Chisago' grape and 'Nokomis' grape. The dimension of the berries along the longitudinal axis of the 'Chisago' and 'Nokomis' grapes are generally smaller at 0.4375 inch (about 11 mm) to 0.5 inch (12.7 mm) along the longitudinal axis and 0.5 inch (12.7 mm) to 0.75 inch (about 19 mm) along the transverse axis. The weight of 'Franconia' berries were observed to be 0.08 ounces (about 2.3 grams) to 0.19 ounces (about 5.4 grams). By comparison, the weight of the 'Chisago' and 'Nokomis' berries are known to be slightly smaller at 0.07 ounces (about 2 grams) to 0.14 ounces (about 4 grams). The 'Franconia' vines are generally less susceptible to powdery mildew and downy mildew than Nokomis, and similar in general disease resistance to Chisago.

SUMMARY OF THE INVENTION

The present invention relates to a new and distinct cultivar of grapevine plant botanically known as *Vitis* hybrid 'Franconia', referred to hereinafter by its cultivar name, 'Franconia'. The 'Franconia' grapevine has a unique combination of hardiness, vigor, disease resistance, and wine quality not found in existing grape varieties known to the Inventors. Moreover, 'Franconia' produces clusters of large grapes that are beneficial to commercial production. Additionally, grapes produced from the 'Franconia' vine have high sugars coupled with increased acidity, which can result in wines with a more complex mouthfeel, and be particularly useful in balancing fortified wines with relatively high alcohol content.

Fruit of 'Franconia' can be fermented to produce red wine having a deep red color and desirable aromas of black currant, cherry and plum. The wine lacks "foxy" aromas typically associated with *V. labrusca*. It also lacks herbaceous aromas that are commonly associated with *V. riparia*. The fruit at harvest is usually comparable in sugar and acidity to wines associated with *V. vinifera*.

When grown in east central Minnesota, the plants of 'Franconia' are extremely vigorous and winter hardy to at least −40 degrees F. (−40 degrees C.). The vines are moderately resistant to herbicide injury and moderately susceptible to foliar phylloxera (*Daktulospahira vitifoliae*) damage. The disease black rot, caused by *Guignardia bidwellii*, has been observed sporadically and at very low levels on the leaves, but not on the fruit. Downy mildew, caused by *Plasmopara viticola*, has been observed at very low levels on the foliage, but has not been seen on the fruit. Powdery mildew disease, caused by *Uncinula necator*, has been seen at very low levels on the foliage, but not on the fruit.

'Franconia' vines set a relatively heavy crop load from year to year that varies with pruning technique. The fruit are borne on tight, large clusters. The berries are relatively large in size and blue-black in color with a light waxy bloom at maturity. The berries have not been observed to split, even under wet conditions in the autumn.

BRIEF DESCRIPTION OF THE DRAWINGS

The accompanying color photographs show characteristics of 'Franconia' grown under typical field conditions in east central Minnesota. The photographs depict the color features as true as is reasonably possible.

DETAILED BOTANICAL DESCRIPTION

Figure 1:
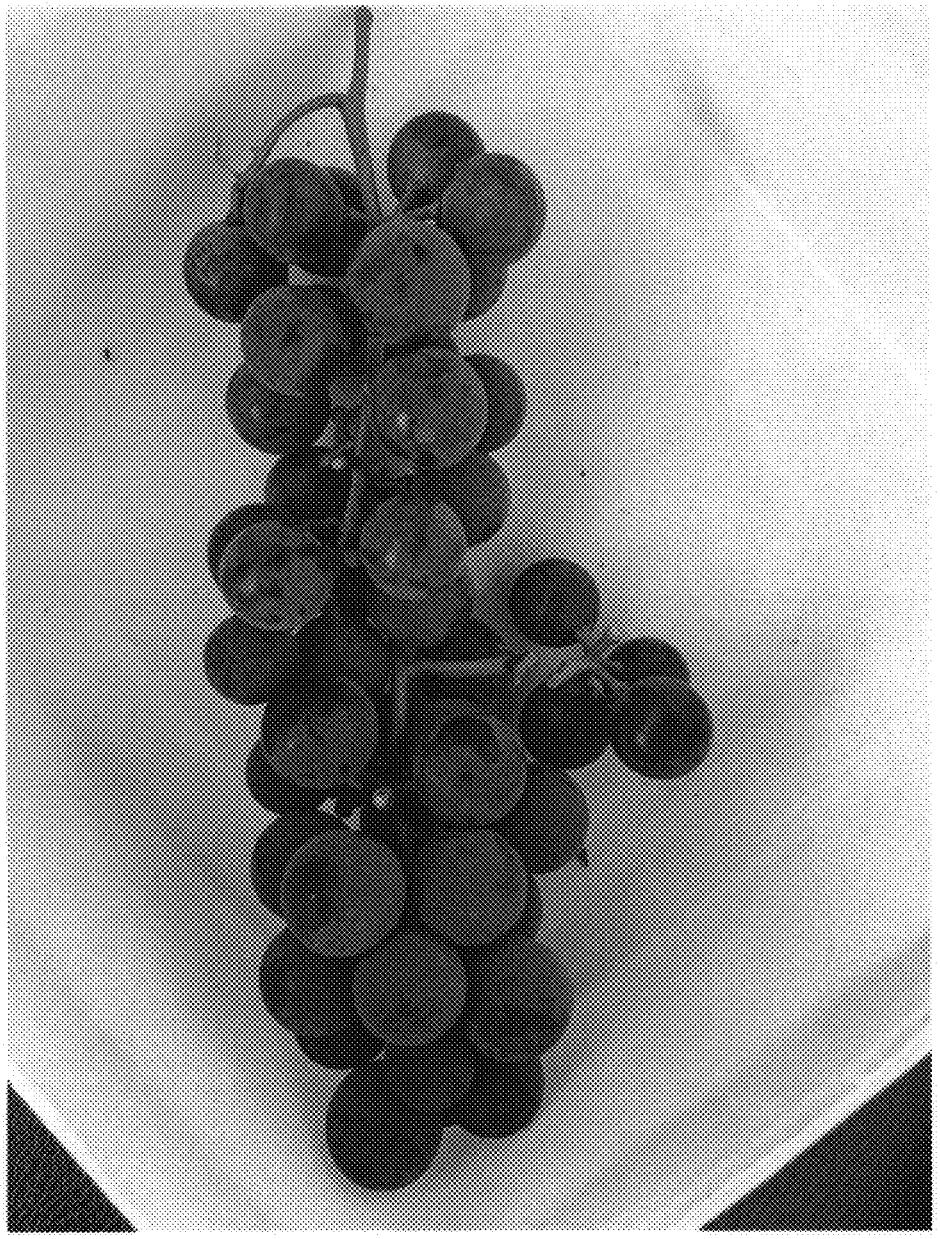
FIG. 1. shows a close-up photo of a fruit cluster of 'Franconia' in late September.
Figure 2:
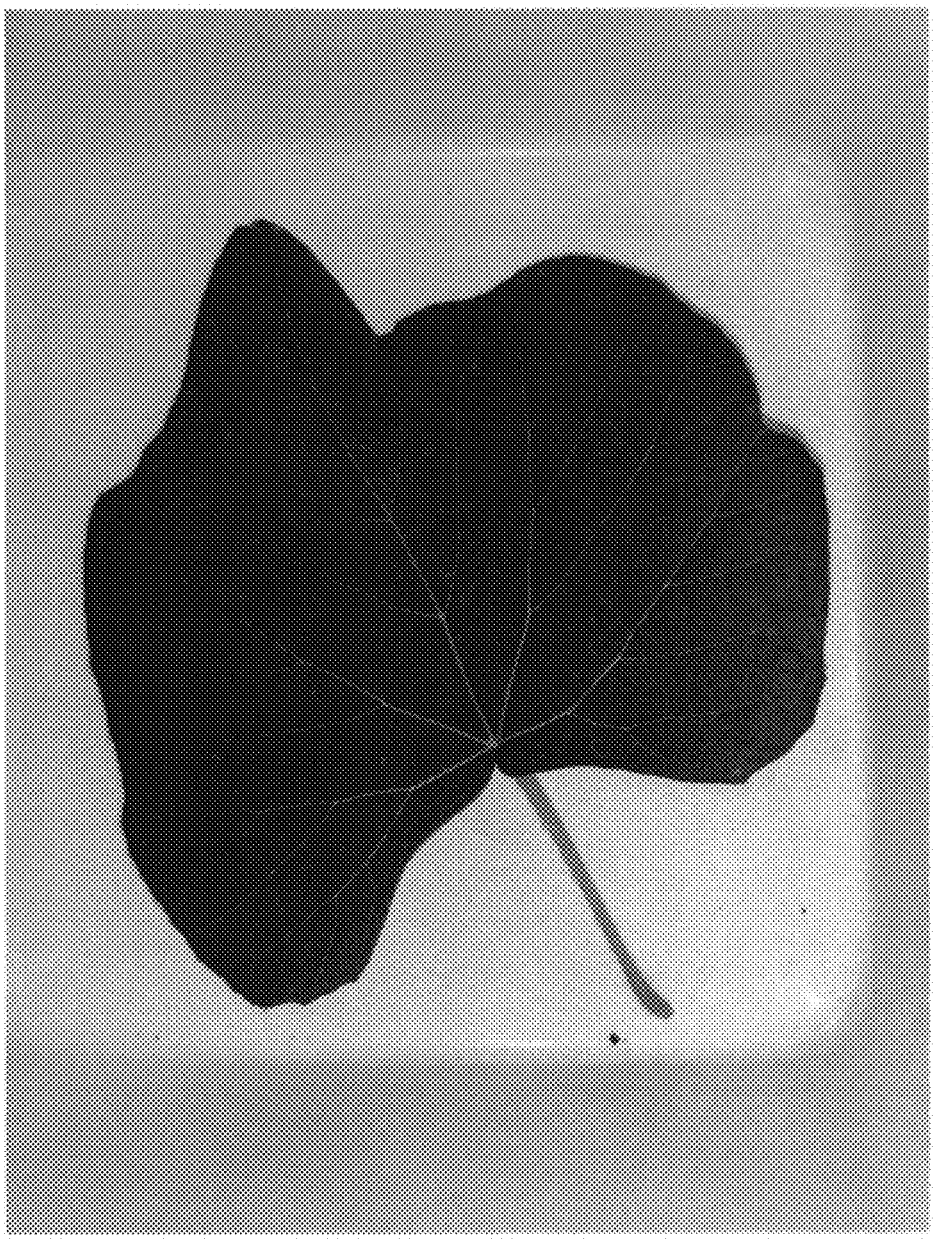
FIG. 2. shows a mature leaf, upper surface in late September.
Figure 3:
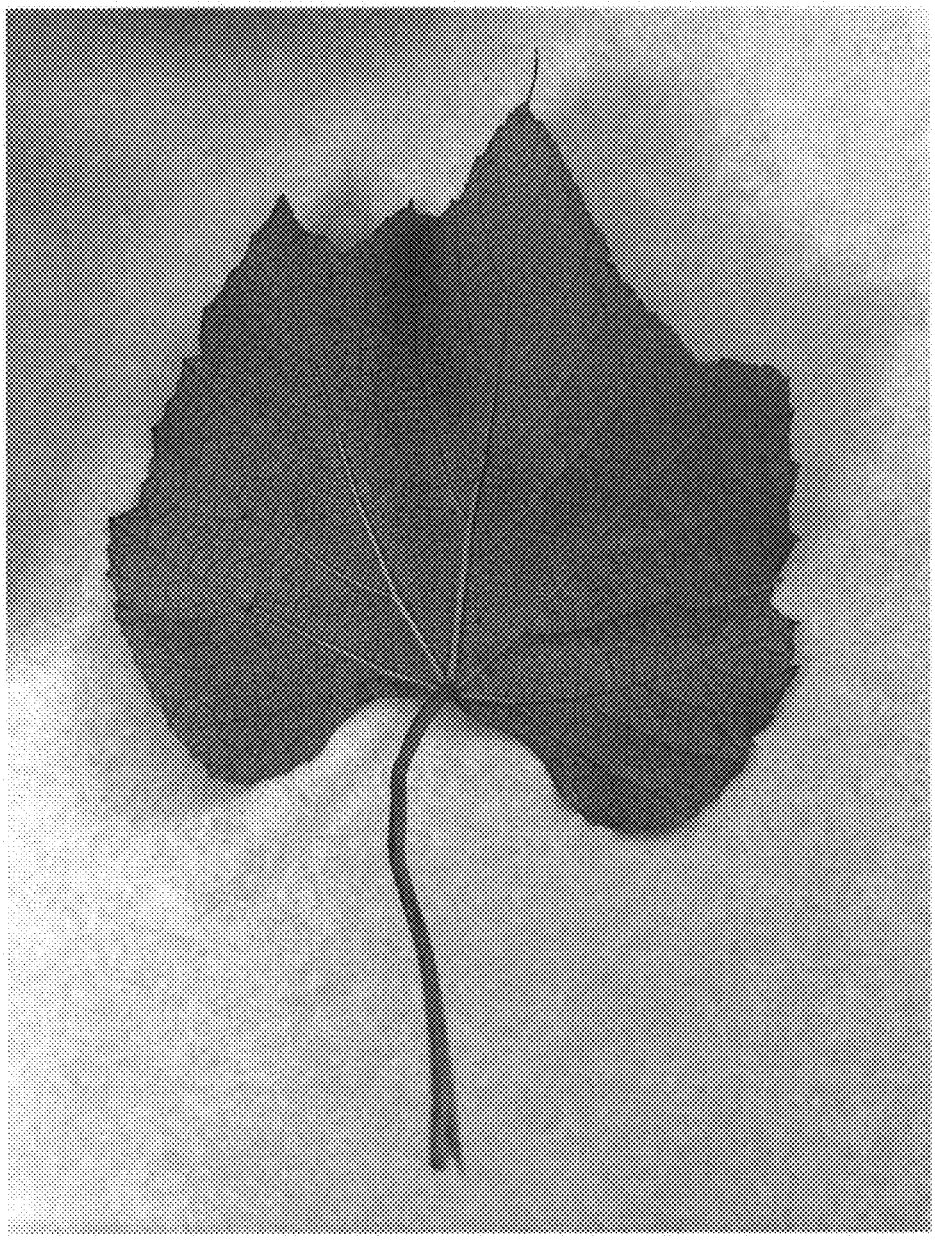
FIG. 3. shows a mature leaf, lower surface in late September.
Figure 4:
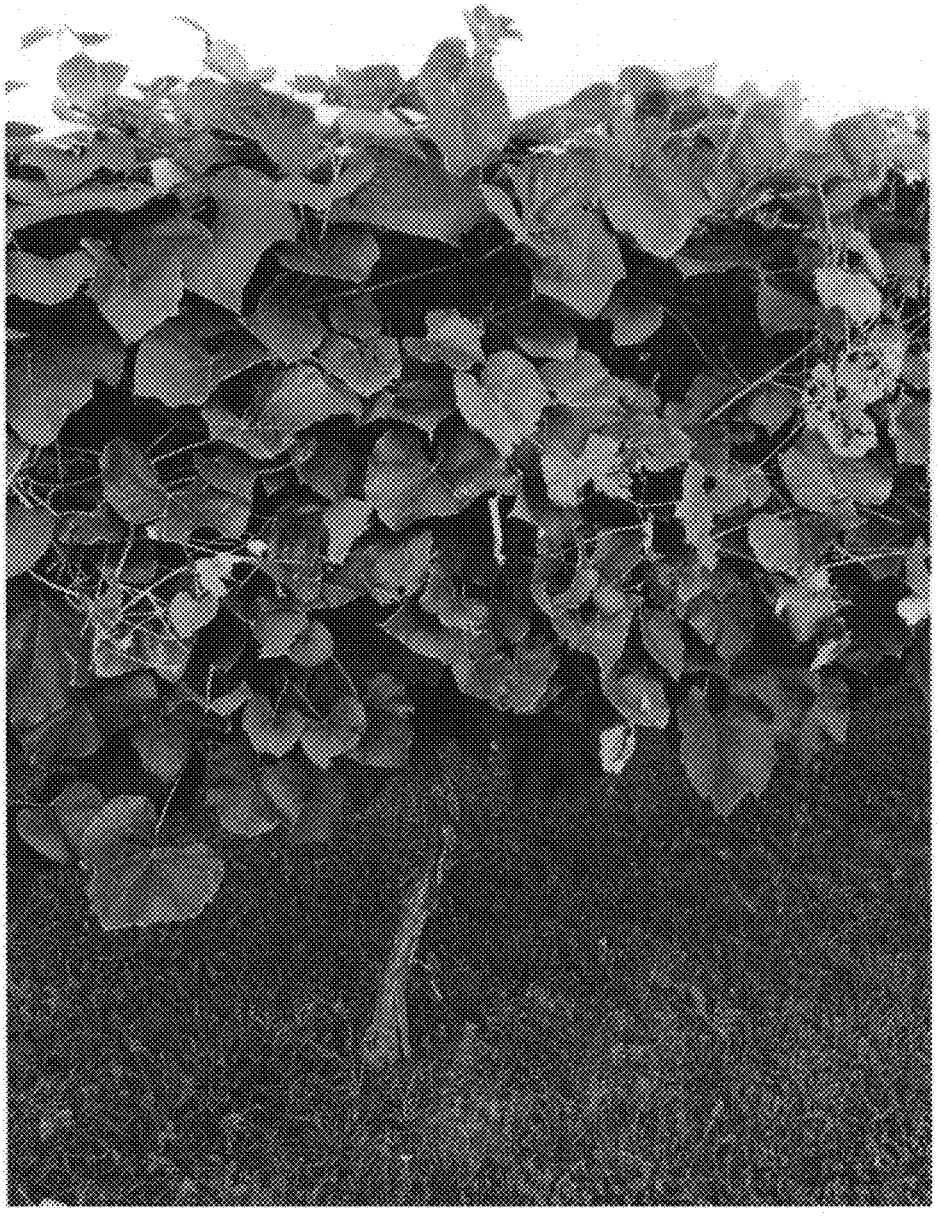
FIG. 4. shows a mature vine in late September.
Figure 5:
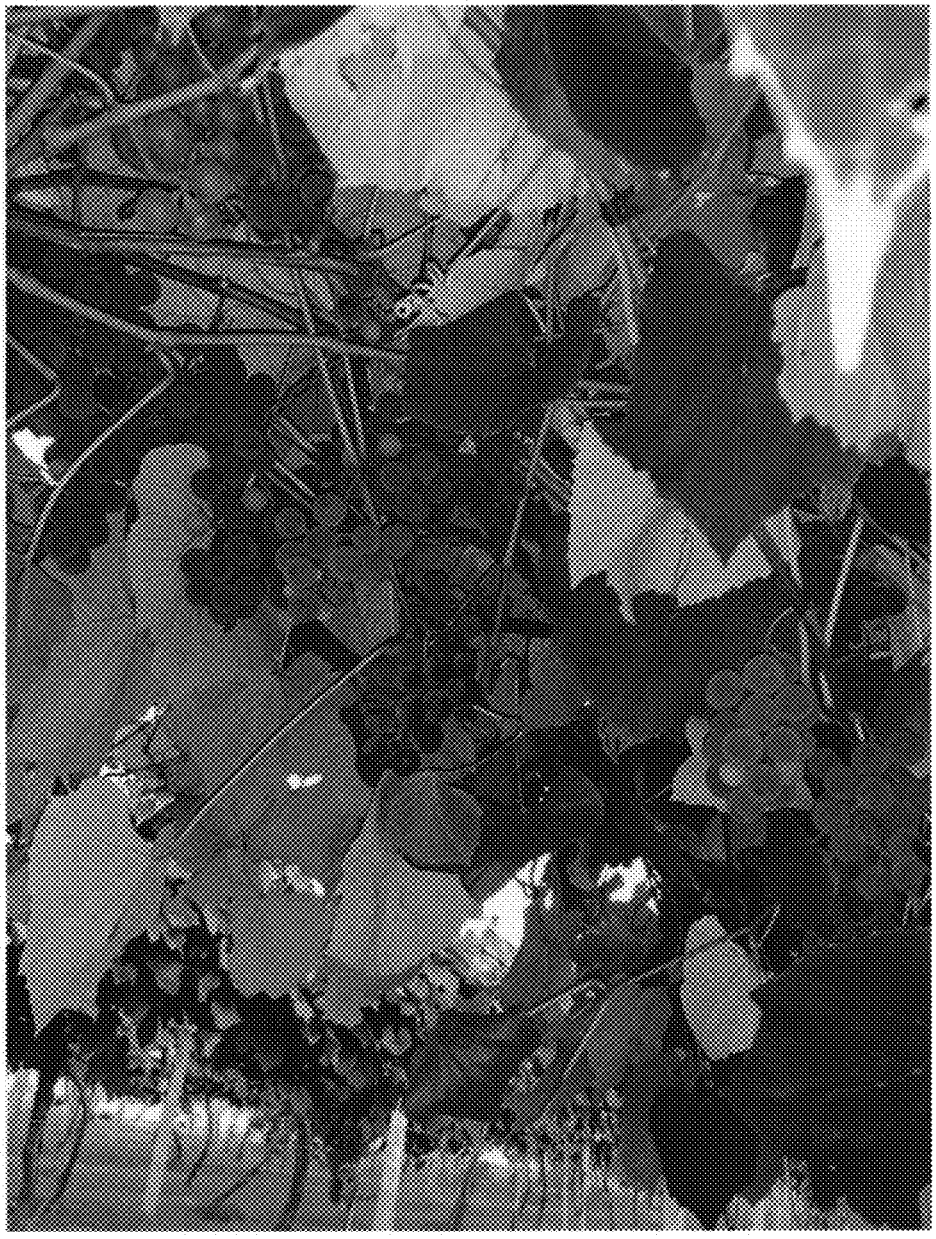
FIG. 5 shows an alternative image of a mature vine in late September.
Figure 6:
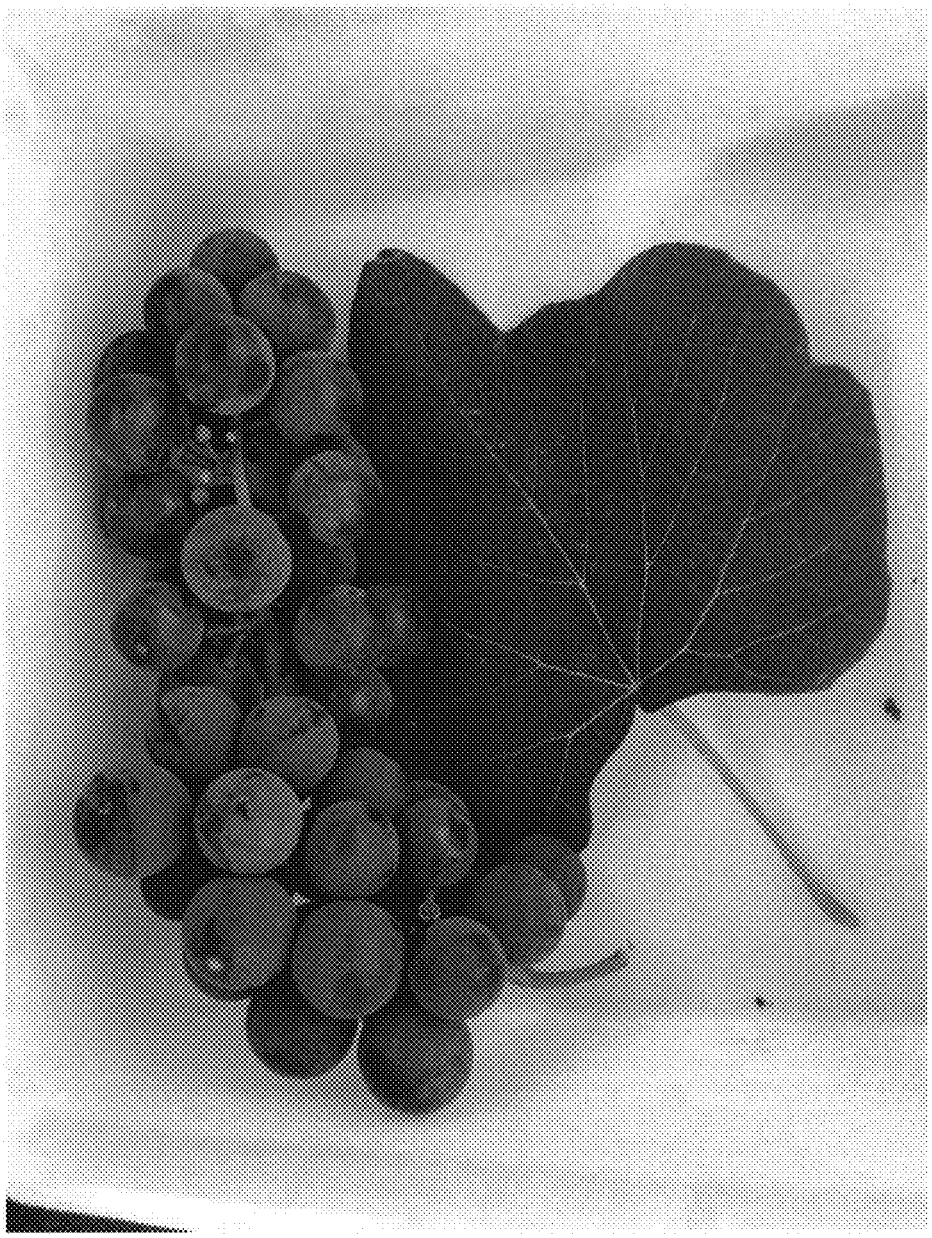
FIG. 6 shows a mature fruit cluster of 'Franconia' alongside a mature leaf in late September.

'Franconia' was selected for its combination of good winter hardiness, vigor, grape size, disease resistance and overall suitability as a red wine grape. It arose as a result of the inventors' grape breeding program to develop commercially viable wine grape varieties to complement non-grape wines produced at their winery.

The grapevine of the present invention was discovered by the inventors among a number of cross combinations in the breeding program. The breeding program produced several test seedlings which were evaluated for their characteristics related to a variety of considerations including, but not limited to, hardiness, vigor, disease resistance, and commercial potential as a wine grape variety. The grapevine was discovered in a controlled cross of the grape 'St. Croix' (U.S. Plant Pat. No. 4,928) ('ES114' (not patented) times 'Seyval' (not patented)) times ('Minn 78' (not patented) times 'Seneca' (not patented)), which was the female parent, and the grape 'Nokomis' (U.S. Plant Pat. No. 23,376), which was the male parent. The inventors have identified the present variety as 'KP 76' and selected the name 'Franconia' therefor. Grapes produced from the 'Franconia' vine have an intense fruit forward flavor and high sugars balanced with increased acidity, which can result in wines with a more complex mouthfeel, and be particularly useful in making fortified wines with relatively high alcohol content.

The inventors have asexually reproduced the present variety in Chisago City, Minn. by means of cuttings, and have carefully observed the variety for approximately 6 years. The following data pertains to vines grown in Chisago City, Minn. Alphanumeric color designations refer to values based on The 2015 R.H.S. Color Chart published by The Royal Horticultural Society, London, England. Many of the descriptors are based on those set forth by the International Board for Plant Genetic Resources in collaboration with the Office Internationale de la Vine et du Vin (OIV) and the International Union for the Protection of New Varieties of Plants.

When dimensions, sizes, colors and other characteristics are given, it is to be understood that such characteristics are approximations set forth as accurately as possible. Variations of the usual magnitude incident to climatic factors, fertilization, pruning, pest control and other cultural practices are to be expected. Botanical Classification: Cultivar of *Vitis* with ancestry tracing to several species including *V. labrusca* and *V. riparia*. Parentage: 'St. Croix' (female), 'Nokomis' (male).

Plants of 'Franconia' are stable and reproduced true to type in successive generations. 'Franconia' has perfect flowers containing extended stamens with anthers having viable pollen. When ripe, the berries of 'Franconia' are blue-black in color 202A with 98D bluish bloom.

The present invention has been shown to be winter hardy to at least −40 degrees F. (−40 degrees C.) in Chisago City, Minn. By way of comparison, the grapevine 'Franconia' is slightly more winter hardy than its female parent, 'St. Croix', which is hardy to about −32 degrees F. (about −35.6.degrees C.). By, contrast, 'Franconia' is about as winter hardy as its male parent, 'Nokomis', which is hardy to about −40 degrees F. (about −40 degrees C.). The values presented below are means (with ranges in parentheses) from vines observed during the 2018 growing season.

Vine:

*Size and vigor*.—Size. — Vines are large and grow best in rows with 8 feet (about 2.4 meters) of spacing between vines. Vigor. — Vigorous — new vines propagated from cuttings were established in a greenhouse on Mar. 3, 2017 and transplanted to a new vineyard located in Chisago City, Minn. on May 17, 2017. Over 75% of the new vines grew at least 4 feet (about 1.2 meters) by Sep. 1, 2017. The inventors have also found it beneficial to train the vine to grow only a single trunk to reduce crowding due to plant vigor in a given growing season.

*Productive capacity*.—In vineyards located in Chisago City, Minn., 'Franconia' vines in experimental plots have consistently produced 9.00 Kg/vine or the equivalent of 5.9 tons of ripe fruit per acre. Canes. — Canes are medium length 5' (about 152 cm) to 10' (about 305 cm). Color of canes. — Brown; 175A, 175B, 175C. Thickness of canes. — Medium. Average width at node is 0.5 inch (about 15.2 cm). Diameter at base. — 3.1 inches (about 7.9 cm) to 4.7 inches (about 11.9 cm). Diameter at midpoint. — 1.9 inch (about 4.8 cm) to 3.5 inch (about 8.9 cm). Typical observed internode cane length 4" (about 10.2 cm) to 12" (about 30.5 cm). Cane surface texture. — Smooth (both mature and immature canes). Shoots. — Length of shoots: medium to long, approximately 6.5 inches (about 16.5 cm). Internode length: approximately 3 inches (about 76 mm). Width at node — approximately 0.5 inches (12.7 mm). Shape — predominately circular. Diameter — approximately 9 mm. Contour — smooth. Color of shoots 144A, 144B, yellow-green. Growing tip. — Generally hang over wires. Tendrils. — Length of tendrils: 4 inches (10.16 mm) to 7 inches (17.78 mm). Texture of tendrils: smooth. Color of tendrils 166A, 166C. Typical and observed tendril diameter: 1 mm to 4 mm. Typical and observed tendril shape: round. Buds. — Shape of buds: pointed. Size of buds: medium, approximately 4 mm times 5 mm. Position of buds — markedly held out at approximately 45 degree angle. Cane bud fruitfulness — basal most fruitful. Bud color: 166B. Bud break: near Chisago City, Minn., bud break is during the middle of May. Trunk. — Bark texture — moderately flaky, small vertical segments approximately 0.40 cm times 6.0 cm. Bark color: striated, 201C and 201D. Leaves: Ten representative mature leaves from different vines were examined during the 2017 and 2018 growing seasons. The leaves were pressed and dried for later analysis. The values presented below are ranges from collections during August of each year. Length of mature leaf. — 4 inches (101.6 mm) to 7 inches (177.8 mm). Width of mature leaf — 3.5 inches (88.9 mm) to 6.5 inches (165.1 mm). Leaves. — Shape. — Cordiform (heart shaped); inferior lateral sinuses and superior lateral sinuses deep with an approximate 1:1 length to width ratio. Apex. — Pointed. Base. — Rounded. Number of lobes. — 3. Anthocyanin coloration of main veins on the upper side of the blade. — Very weak — red 59C. Mature leaf profile. — Flat. Blistering surface of blade upper surface. — Absent. Leaf blade tip. — In the plane of the leaf Margins. — Serrate with irregular teeth. Height of teeth on margin (average). — 0.31 cm (ranges from 0.2 cm to 0.9 cm; height/width ratio is approximately 0.25 (ranges from 0.10 to 0.43). Shape of teeth on margin. — Wide teeth with convex sides. Texture (mature leaf). — Upper surface: Smooth to slightly bullate; glabrous. Lower surface: Smooth; almost glabrous with sparse short hairs on veins. General shape of petiole sinus. — Slightly open. Tooth at petiole sinus. — Absent. Petiole sinus limited by veins. — Absent. Shape of upper lateral sinus. — Lobes slightly overlapping. On mature leaf, petiole sinus is 1.47 inches (3.7 cm) long and 0.52 inches (1.3 cm) wide at widest point. Autumn coloration of leaves. — Near grayed-yellow 162A on upper leaf surface, near yellow-green 153D on lower leaf surface. Coloration is slow to develop. Normally frost kills leaves before extensive color change. Texture of upper surface of leaf — Smooth. Texture of lower surface of leaf. — Rough. Length of petiole. — 4 inches (101.6 mm) to 5 inches (127 mm). Shape of petiole. — Mostly round. Diameter of petiole. — 3.1 mm. Color of petiole. — 145A. Color of adaxial leaf surface. — 146A, 146B, yellow-green leaf surface. Color of abaxial leaf surface — 46C, yellow-green leaf surface. Pubescence very sparse on main veins abaxial surface and at petiolar junction. Color of leaf veins. — About 146A on upper surface, about 146B, yellow-green on lower surface. Flowers: Flower sex. — Hermaphrodite. Fragrance. — Moderately fragrant. Date of bloom. — Late May when grown in Chisago City, Minn. Date of full bloom. — Early June when grown in Chisago City, Minn. Type. — Fertile, based on use in controlled crosses. Amount of pollen. — Abundant. Color of pollen. — 4B, yellow. Petals are ovoid in shape, cohering at summit and separating at base. — 2.5 mm long; 1 mm wide at fused end; reflexed after dehiscence. Flower petals are typically five in number, and open from the bottom to the top and remain entire after separation. Apex of petals is concave. Base is smooth and about 2.4 mm in circumference. Margins are smooth and convexly curved. Shape of cluster. — Slightly conical. Average floral cluster length. — 6.5 inches (16.5 cm). Average floral cluster diameter. — 4.0 inches (10.2 cm). The values presented below are means (with ranges in parentheses) from vines observed during the 2018 growing season. Number of flowers per cluster 98 (72-127). Size of individual flower. — 5.2 mm long, 3.9 mm wide. Color of stamen. — Anther: 162C, grayed yellow. Color of filament. — 155A, white. Number of stamen. — 5.0 (4-6). Number of pistil. — 1 per flower. Length of pistil. — 2.4 mm. Color on upper surface of petal. — 145A, yellow-green. Color on lower surface of petal. — 149D, light green. Sepals. — Five in number, and generally very poorly developed. Color of sepal. — 144A, yellow-green (both surfaces). Color of pistil. — 144A, yellow-green. Cluster peduncles. — Length 1.2 inches (3 cm) to 3.5 inches (9 cm), diameter 0.8 inches (2.0 cm) to 2.4 inches (6.0 cm). Cluster peduncle color. — 141A, light green. Texture of peduncles. — Smooth, glabrous. Fruit: Maturity. — Ripe for commercial harvesting and wine approximately mid September near Chisago City in east central Minnesota. Solids. — Sugar: medium brix (19.5% to 26.3%). Juice pH. — (3.15-3.47). Percent titratable acidity. — (0.70-0.95%). The values presented below are means (with ranges in parentheses) from fruit observed in the 2018 growing season. Seeds. — Seeds: 2-4 seeds per berry. Seed length: 0.55 mm (0.50-0.55) to 0.63 mm (0.54-0.65). Seed width: 0.33 mm (0.31-0.36) to 0.39 mm (0.35-0.46). Seed weight: 0.020 g. to 0.033 g. Seed Color: 165A, 177A. Clusters. — Generally the 'Franconia' grape produces medium-sized clusters weighing 0.4 pounds (about 181 grams) to 0.8 pound (about 363 grams). By comparison, the clusters of "Franconia" are similar in weight to 'Nokomis' and much heavier than 'Chisago' which are 0.2 pounds (about 91 grams) to 0.5 pounds (about 227 grams). Clusters of 'Franconia' are tight and form a conical shouldered cluster. Size of cluster. — 9.8 cm long (7.3-13.7); 4.9 cm wide (3.4-6.6). Between 37 and 56 berries are included in a typical cluster. This is slightly less than both 'Chisago' which generally has 40 to 70 berries in a typical cluster and 'Nokomis' which generally has 45 to 90 berries in a typical cluster. Clusters per plant. — 10.5. Clusters per shoot. — 2.3 clusters per shoot. Pedicel length ranges from 0.32 inches (8.0 mm) to 0.52 inches (13.0 mm). Pedicel diameter ranges from 0.06 inches (1.5 mm) to 0.1 inches (2.5 mm) at mid-pedicel. Pedicel texture — smooth, glaborous. Pedicel color — grayed-yellow 162A. The berry attachment is very strong. Almost no shatter occurs at full maturity. Berries. — Berry size is medium-large and berry form is uniform. For example, the dimension of berries along the longitudinal axis is 0.5132 inch (about 13 mm) to 0.75 inch (19.1 mm). The dimensions of 'Franconia' berries along the transverse axis is 0.6 inch (15.24 mm) to 0.82 inch (about 21 mm). By comparison, these berry dimensions are larger than both the 'Chisago' grape and 'Nokomis' grape. The dimension of the berries along the longitudinal axis of the 'Chisago' and 'Nokomis' grapes are generally 0.4375 inch (about 11 mm) to 0.5 inch (12.7 mm) along the longitudinal axis and 0.5 inch (12.7 mm) to 0.75 inch (about 19 mm along the transverse axis. Berry weight. — The weight of 'Franconia' berries were observed to be 0.08 ounces (about 2.3 grams) to 0.19 ounces (about 5.4 grams). By comparison, the weight of the 'Chisago' and 'Nokomis' berries are known to be smaller at 0.07 ounces (about 2 grams) to 0.14 ounces (about 4 grams). — Round. Skin thickness. — Medium. Firmness. — Firm. Tendency to split. — None. Color. — 202A black with 98D bluish bloom. Color of flesh 63C light pink. Flavor. — Sweet crisp. Eating quality. — Good. Use. — Wine, juice. Shipping and handling qualities. — Excellent. Keeping quality. — After two months in cold storage, still in good appearance. Vineyard performance: Based on observations compiled over 4 years (2015-2018). Susceptibility to powdery mildew (*Uncinula necator*). — Low — similar to 'Chisago' and less susceptible than 'Nokomis'. Susceptibility to downy mildew (*Plasmopara viticola*). — Moderate. Susceptibility to black rot (*Guignardia bidwellii*). — Low — similar to 'Chisago' and less susceptible than 'Nokomis'. Susceptibility to foliar phylloxera (*Daktulospahira vitifoliae*). — Moderate. Susceptibility to crown gall (*Agrobacterium*). — No natural infection observed. Susceptibility to phenoxy herbicide drift. — Low. Winter hardiness. — Trunks have survived −40.degree. F. (−40.degree. C.). Wood ripening. — Good. Wine quality: Descriptions below are compiled from observations on wine made from 'Franconia' fruit harvested during the 2016-2017 growing seasons. 1. Flavors and aromas: black currant, cherry, plum; no herbaceous aroma or very slight *V. labrusca* aroma. 2. Balance: medium body, well balanced when finished dry or with residual sugar. 3. Color: attractive deep red color. 4. Propensity for oxidation: low. 5. Overall quality: excellent.

The invention claimed is:

1. A new and distinct variety of grapevine plant designated 'Franconia' as illustrated and described herein.

* * * * *